United States Patent

Vahaviolos

[11] 4,090,400
[45] May 23, 1978

[54] METHODS AND APPARATUS FOR THE NON-DESTRUCTIVE TESTING OF BONDED ARTICLES

[75] Inventor: Sotirios John Vahaviolos, West Windsor Township, Mercer County, N.J.

[73] Assignee: Western Electric Company, Inc., New York, N.Y.

[21] Appl. No.: 788,568

[22] Filed: Apr. 18, 1977

[51] Int. Cl.² .................................... G01N 29/00
[52] U.S. Cl. ................................. 73/88 B; 73/582
[58] Field of Search ............... 73/88 B, 150 A, 88 R, 73/71.5 R, 67.2

[56] References Cited

U.S. PATENT DOCUMENTS

| 3,531,982 | 10/1970 | Clotfelter et al. | 73/67.2 |
| 3,605,486 | 9/1971 | Anderholm et al. | 73/88 B |
| 3,924,456 | 12/1975 | Vahaviolos | 73/88 R |

Primary Examiner—Jerry W. Myracle
Attorney, Agent, or Firm—D. J. Kirk

[57] ABSTRACT

A beam lead device which has been thermocompressively bonded to a substrate is non-destructively tested to determine the strength thereof by directing a short burst of air at the device and detecting the Stress Wave Emission (SWE) signals emanating from the bond site subsequent to said burst of air. The SWE signals are then processed to determine the strength of the adhesion bond.

9 Claims, 4 Drawing Figures

METHODS AND APPARATUS FOR THE NON-DESTRUCTIVE TESTING OF BONDED ARTICLES

BACKGROUND OF THE INVENTION

1. Field of the Invention

The instant invention is directed to evaluating the strength of adhesion bonds. In particular, non-destructive bond strength tests are accomplished on the bonded articles using Stress Wave Emission techniques.

2. Description of the Prior Art

The instant invention will be described in relation to the non-destructive testing of beam lead devices. However, it will be appreciated that the instant method can be advantageously used to test various types of connections such as crossovers, lead frame bonds or the like.

Beam lead devices have a central body or chip portion with a plurality of laterally extending beam leads. These leads are thermocompressively bonded to metallic bonding pads on insulative substrates having conductive patterns thereon. Such a bonding technique results in the leads being firmly attached to the metallic pads while the chip portion thereof is spaced from the substrate.

Once bonded, the strength of such adhesion must be determined prior to further assembly. A number of tests have been devised in order to make such a strength determination. One such test provides a hook or a clamp to grasp the chip and apply a predetermined upward force to the device. Additionally, an upward force may be applied with an air blaster having at least a pair of opposed air ducts which simultaneously direct air beneath the chip portion as described in U.S. Pat. No. 3,759,088 which issued on September 18, 1973 to N. E. Hardwick III. The opposed impinging air jets induce a predetermined resultant force on the underside of the chip portion causing poorly bonded devices to be torn away from the substrate. However, with these testing techniques, the results are conclusive only if most of the leads are unsoundly bonded and the device torn away from the substrate. Such a test cannot readily identify situations in which only one or two of the perhaps sixteen beam leads are poorly bonded. If only a few leads are unsoundly bonded, the device would not be torn away from the substrate, for the sound bonds would tend to hold the device in place.

Another technique commonly used is to apply a continuous peel force to a small percentage of devices in a particular lot. The applied force continues until the devices peel away from the substrate and such force is recorded. If less than a predetermined small percentage of devices fail below an acceptable peel force value, the entire lot is regarded as acceptable; if the percentage of devices failing is unacceptable, the entire lot is discarded. Such destructive testing is not entirely satisfactory due to the expense associated with the loss of product which must be destroyed during testing and the inherent uncertainty which is associated with such statistical testing.

Another testing technique described in U.S. Pat. No. 3,559,054 which issued to R. W. Bowers on Jan. 26, 1971, directs a high velocity air blast at a device while simultaneously monitoring changes in electrical resistance of the bonded joint connecting the device to the substrate. Such a technique requires a substantially continuous blast of air which can blow the device from the substrate.

A further method and apparatus for non-destructively evaluating the strength of a bond in real time is set forth in U.S. Pat. No. 4,004,456 which issued on Jan. 25, 1977 to S. J. Vahaviolos and is assigned to the instant assignee. This patent teaches the measuring of stress wave emissions emanating from the bonding site during the compression phase of the formation of an adhesion bond and compares this measurement with a predetermined substantially linear relationship between the emitted stress wave energy and the strength of the bond. Although such a method is quite effective for determining the bond strength during the formation of a bond, it is inapplicable for testing bond strengths after the bond has been made.

Accordingly, there is a need for a fast, accurate non-destructive test of bond strength subsequent to adhesive bonding.

SUMMARY OF THE INVENTION

The instant invention has overcome the foregoing problems with a non-destructive test method of measuring the strength between adhesively bonded articles, wherein at least a portion of one of the bonded articles is normally spaced from the other article. The method is characterized by the steps of applying a short duration burst of energy to the spaced portion of at least one of the bonded articles, detecting the stress wave emission signals emanating from the bond site subsequent to said energy burst, and comparing the detected stress wave emission signals with a predetermined acceptable stress wave value to determine the strength of the bond.

Advantageously, the short duration burst of energy can be generated by various apparatus such as an air jet, laser beam or the like which can provide low mechanical impact forces which will not deleteriously affect the bonded articles.

DETAILED DESCRIPTION OF A PREFERRED EMBODIMENT

The instant invention will be described in relation to the non-destructive testing of beam lead devices. However, it will be understood that such description is exemplary only and is for the purposes of exposition and not for the purposes of limitation. It will readily be appreciated that the inventive concepts as described are equally applicable to any type of adhesion bond wherein a portion of one of the bonded articles extending from the bond site is spaced from the other article and may be induced to vibrate (i.e., crossovers, lead frame connections, or the like) by providing a sudden mechanical impact thereto.

Figure 1:
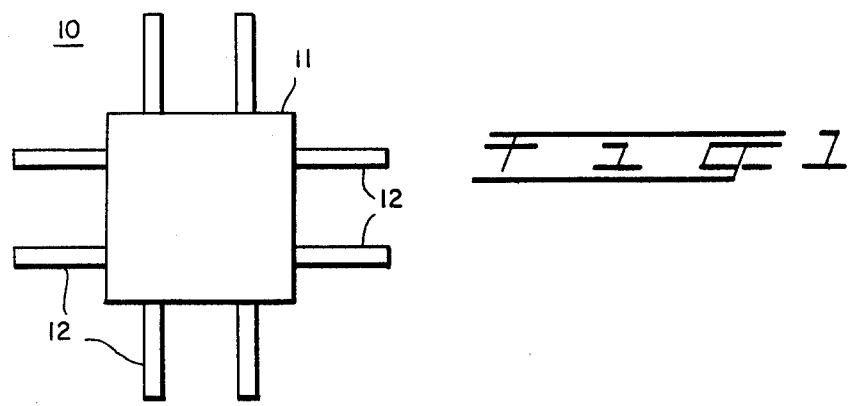
FIG. 1 is a plan view of a beam lead device.

A plan view of a beam lead device, generally referred to by the numeral 10 in FIG. 1 has a body or chip 11 portion having selected doped areas therein to form circuit components. A plurality of cantilevered beam leads 12—12 extend laterally from the chip 11. The overall dimensions of the beam lead device 10 is typically 0.020 to 0.052 inch by 0.017 to 0.037 inch.

Figure 2:
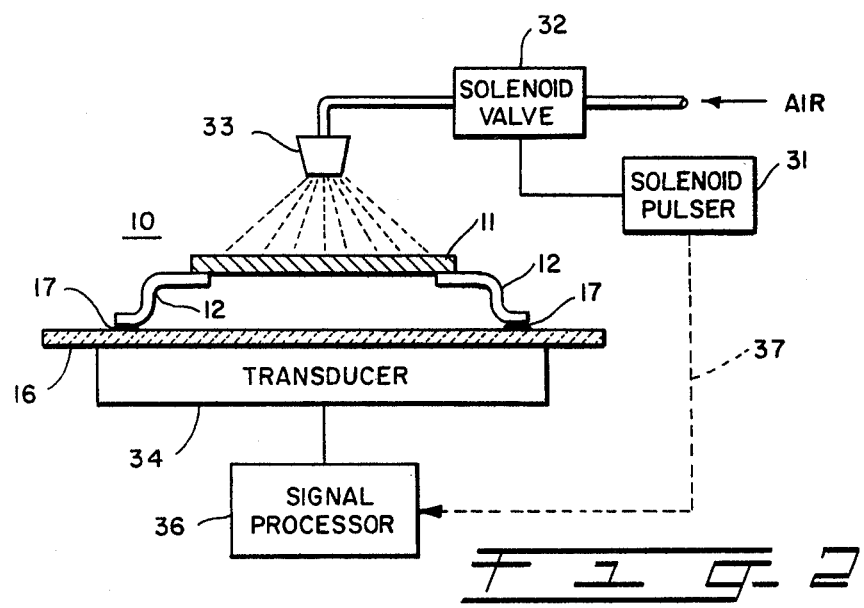
FIG. 2 depicts a beam lead device bonded to a ceramic substrate.

FIG. 2 is a cross-sectional view of a beam lead device 10 bonded to a ceramic substrate 16. The leads 12—12 have a film of conductive material such as gold deposited thereon and the bonding pad 17 on the substrate 16 also has a thin film coating of conductive material which also may be gold. The beam leads 12—12 are bonded to the pads 17—17 by applying heat and pressure for a predetermined period of time with a thermocompressive bonding tool which is well known in the art. During bonding the leads 12—12 tend to bend in substantially an "S" configuration as shown in FIG. 2. Such bending causes the chip 11 to be forced upward and remain in spaced relation to the substrate 16. A plurality of such beam lead devices 10—10 may be similarly bonded on a single substrate 16.

Once the beam lead device 10 is bonded to the substrate 16, it is necessary to determine the bond strength prior to further fabrication. As hereinbefore indicated, present techniques for measuring the strength between articles have met with limited success resulting in uncertainty of results and the destruction of acceptable product.

The present invention precludes such uncertainty and destruction of product by a non-destructive test using the exemplary apparatus set forth in FIG. 2. The apparatus includes a solenoid pulser 31, a solenoid valve 32, an air nozzle 33, a transducer 34 and a signal processing circuit 36.

In operation, the solenoid pulser 31 activates the solenoid valve 32 for a short period of time (i.e., from 1 to 10 milliseconds) to permit a single pulse or burst of air to be directed through the nozzle 33 to provide a sudden mechanical impact to the chip 11. Simultaneously, with the operation of the solenoid operated valve 32, an enable signal is forwarded from the pulser 31 to the processor 36 (via dashed line 37) to activate the processor. The impact of the burst of air onto a poorly bonded chip 11 will result in substantial Stress Wave Emissions (SWE) at the bonding pads 17—17 due to cracking, slippage or loose particles which is indicative of the bad bond. However, low level or no SWE signals will emanate from the bonding area at or about the pads 17—17 when a good bond has been produced.

SWE may be defined as the elastic waves which are propagated in a structure as the result of applied force. The emissions have been associated with deformation processes such as dislocation motion, dilocation pile-up breakaway, micro- and macro-cracking as well as slippage and loose particles. U.S. Pat. No. 3,924,456 which issued on Dec. 9, 1975 to S. J. Vahaviolos and is assigned to the instant assignee provides a detailed description of SWE signals and methods and apparatus for detecting such signals.

The transducer 34, mounted under the ceramic substrate 16, monitors the SWE signals emanating from the bond areas, more particularly, those SWE signals emanating from the bond area after the termination of the air impulse. Whenever SWE signals are induced in the area of the bonds, such signals travel through the substrate 16 and excite the sensor 34. Depending on wave damping at the interfaces, the traveling mechanical stress impulse will cause the sensor 34 to provide an output voltage change which is almost proportional to the amplitude of the impulse.

The sensor 34 is a piezoelectric type, such sensors can be divided into two broad categories, i.e., non-resonant and resonant, devices. Non-resonant devices are so named because they are designed to operate well below their natural resonance and over a relatively large frequency range, usually several octaves. Resonant devices, on the other hand, are designed to operate at a single frequency, that is, the mechanical resonant frequency of the device and over a band of frequencies that is usually less than one octave, which band includes the resonant frequency of the resonant device. Both resonant and non-resonant devices can be used to implement the instant invention, however, the resonant device will usually provide high sensitivity.

Sensors comprised of Barium Titanate and Lead Zirconate Titanate have been used in the resonant mode. Also, Lead Metaniobate sensors have been employed where relatively high sensitivity, high working temperatures, and freedom from electrical ringing are desired. All three of the above types of sensors have been employed satisfactorily in the illustrative embodiment of the invention.

Figure 3:
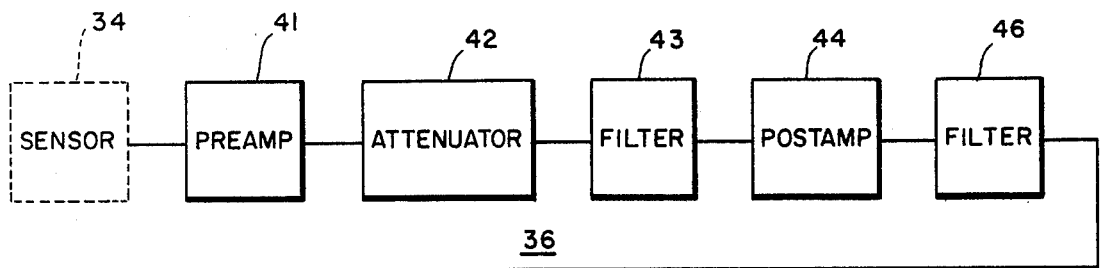
FIG. 3 is a simplified block diagram describing the stress wave emission detection circuitry.
Figure 3:
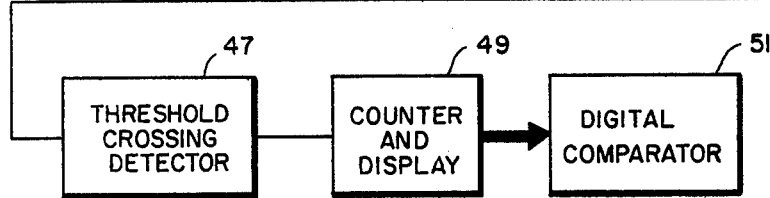

The SWE signals are forwarded from the transducer 34 to the signal processing circuit 36. Various types of SWE signal processing circuitry are known (i.e., the aforementioned U.S. Pat. No. 3,924,456), however, a particularly effective processing circuit 36 used in the exemplary embodiment is shown in block diagram form in FIG. 3. The transducer 34 is serially connected to a preamplifier 41, an attenuator 42, a first filter 43, a post-amplifier 44 and a second filter 46. The output of the second filter 46 is connected to both a threshold crossing detector 47 which forwards a digital output signal to a counter and display circuit 49 which, in turn, is connected to a digital comparator circuit 51.

The SWE signal, sensed by the transducer 34, after the termination of impulse of air, is forwarded to the preamplifier 41 which is required due to the low amplitude of the SWE signal. The preamplifier may be any well-known type which provides a high gain (i.e., 1000x) with a narrow frequency band (i.e., 0.6 to 1.0 NHz) with a sensitivity of $4\mu$ volts and above. The preamplifier 41 may be mounted external to the signal processing circuitry and located as close as practicable to the transducer 34 to minimize cable capacitance effects. The attenuator 42 is used to prevent saturation of subsequent processing circuits and is of the variable type having a 50 ohm in, 50 ohm out impedance with a three-position selection of 0, $-10db$ and $-20db$ attenuation. The first filter 43 may be a well-known high pass Butterworth filter having a cutoff frequency above 300 KHz (about twice the mechanical natural frequency of the device under test). The post-amplifier 44 may be any well-known high speed operational amplifier having a variable gain.

The filter 46 should be a high pass filter circuit having a 500 to 600 KHz high pass response. One such filter 46 is schematically described in "Integrated Electronics Analog and Digital Circuits and Systems" by Millman et al. published by McGraw Hill, 1972, page 552, FIG. 16-19. The filter makes use of Teledyne Philbric TP-1322 operational amplifiers and has a high pass response above 500 to 600 KHz.

The threshold crossing detector 47 will provide a single digital pulse output for each positive-going crossing of the SWE signal through a preset threshold value. The digital pulses are forwarded to the counter and display circuit 49 which counts the number of pulses and visually displays the count. The digital count from circuit 49 is forwarded to the digital comparator 51 which compares the count to a preset acceptable value.

Figure 4:
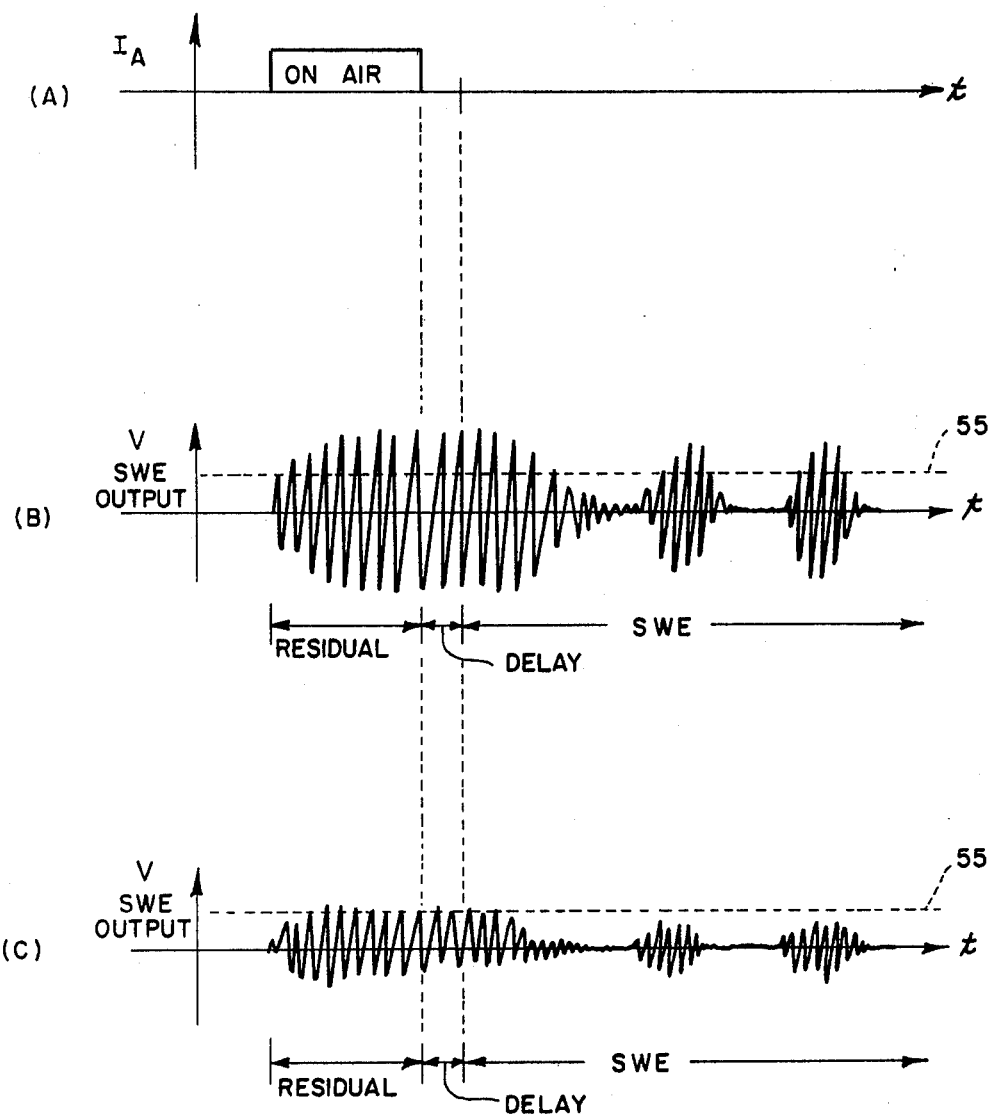
FIG. 4 shows curves representative of stress waves emanating from a device under test.

Accordingly, in operation a sudden mechanical impact is imparted to the chip 11 by the air impulse passing through the nozzle 33 having an opening about one mil in diameter and spaced about one inch above the chip 11. The SWE signals are monitored by the processing circuit 36 to determine the strength (quality) of the bond. FIGS. 4(B) and 4(C) depict two possible SWE output signals from the second filter 46 while FIG. 4A indicates the time period of the air burst. During the time that the air burst is impacting on the chip 11, the signal output is indicative of the residual stresses that are being relieved due to such impact. Such residual signals have been found to be unreliable in determining the strength of bonds. That portion of the curves in FIG. 4(B) and FIG. 4(C) showing the SWE signals occurring subsequent to the air impulse have been found to be intimately related to the strength of the bond.

It has been discovered that unacceptable or bad bonds will manifest high amplitude SWE signals subsequent to the end of the impulse, which have peaks above a predetermined threshold level 55 as shown in FIG. 4B, while acceptable bonds having relatively low level SWE signals are shown in FIG. 4C. It has been determined that more reliable results are obtained by delaying SWE processing for a short period of time after the termination of the air pulse. Typically, a delay of about one-tenth of the air impulse time has been found to provide adequate results. Such a delay or settling time eliminates any uncertainty as to whether or not subsequent signals are stress waves due to poor bonds or residual stress caused by a non-abrupt cutoff of the air burst.

The threshold crossing detector 47 will forward the digital pulses associated with each positive-going crossing of the threshold value 55 to the counter and display circuit 49 whenever the amplitude of the SWE signal exceeds the threshold. The circuit 49 will count and display the number of pulses counted. The pulse count will also be forwarded to the digital comparator 51 which will compare the count to a predetermined value to determine whether or not the bond is acceptable. The comparator 51 is arranged to provide a go-no-go output signal (audible and/or visual) indicative of the acceptability of the bond strength. Both the value of the threshold 55 and predetermined acceptable count value may differ for different applications and are determined empirically for each application.

Although the exemplary embodiment imparts a sudden mechanical impulse to the beam lead device 10 with a burst of air, the present invention should not be so limited. Other methods using jet impulses of various gases, laser beam pulses or actually physical contacting the chip 11 with a low impact tool is also contemplated. The method of providing the impact is not as important as imparting a relatively low impact force for a short period of time to induce vibratory stresses in bonds having low strength.

Additionally, the exemplary embodiment depicts the testing of a single device 10 on a substrate 16; however, it should be clear that a substrate having a plurality of such devices thereon could be sequentially tested and the SWE output signals time division multiplexed in a well-known manner.

What is claimed is:

1. A method for non-destructively measuring the strength of an adhesion bond between at least two articles wherein at least a portion of one of the bonded articles is normally spaced from the other article, comprising the steps of:
   (a) applying a short duration burst of energy to the spaced portion of one of the bonded articles;
   (b) detecting the stress wave emission signals emanating from the bonded articles subsequent to said energy burst; and
   (c) comparing the detected stress wave emission signals with predetermined acceptable stress wave emission signals to determine the strength of the bond.

2. The method as set forth in claim 1 wherein the step (b) of detecting the stress wave emission signals includes:
   detecting only the stress wave emission signals having amplitude excursions exceeding a predetermined threshold; and
   converting said signals exceeding said threshold to digital pulses.

3. The method as set forth in claim 2 wherein the comparing step (c) is characterized by:
   counting the digital pulses; and
   comparing the counted pulses to a predetermined acceptable threshold value to determine the bond strength.

4. The method as set forth in claim 1 wherein the articles are a beam lead device which has been adhesively bonded to an insulative substrate.

5. The method as set forth in claim 1 wherein the articles are a crossover lead which has been adhesively bonded to an insulative substrate.

6. The method as set forth in claim 1 wherein the first article is a lead frame which has been adhesively bonded to an insulative substrate.

7. Apparatus for non-destructively measuring the strength of an adhesive bond between at least two articles wherein at least a portion of one of the bonded articles is normally spaced from the other article, comprised of:
   means for applying a short duration burst of energy to the spaced portion of the bonded article;
   means for detecting stress wave emission signals emanating from the bonded articles subsequent to said energy burst; and
   means for comparing the detected stress wave emission signals with a predetermined acceptable signal to determine the strength of the bond.

8. The apparatus as set forth in claim 7 wherein the detecting means further comprises:
   means for detecting only the stress wave emission signals having amplitude excursions exceeding a predetermined threshold; and
   means for converting the signals exceeding the threshold to digital pulses.

9. The apparatus as set forth in claim 8 wherein the detecting means further comprises:
   means for counting the digital pulses; and
   means for comparing the counted pulses to a predetermined threshold value to determine the acceptability of the bond strength.

* * * * *